United States Patent
Viart et al.

(10) Patent No.: US 6,589,243 B1
(45) Date of Patent: Jul. 8, 2003

(54) POSTERIOR BACKBONE OSTEOSYNTHESIS DEVICE

(76) Inventors: Guy Viart, 6 Rue de Vaulx, Saint Leger (FR), 62128; Jean-Pierre Freund, 25 Rue Stockholm, Strasbourg (FR), 67000; Jean-Paul Steib, Clos des Vanneaux, 6 Rue des bouvreuils, Strasbourg (FR), 67100; Emeric Gallard, La Vergne, Fenioux (FR), 79160

(*) Notice: Subject to any disclaimer, the term of this patent is extended or adjusted under 35 U.S.C. 154(b) by 0 days.

(21) Appl. No.: 09/786,973
(22) PCT Filed: Mar. 8, 1999
(86) PCT No.: PCT/FR99/02136
§ 371 (c)(1),
(2), (4) Date: Apr. 19, 2001
(87) PCT Pub. No.: WO00/16710
PCT Pub. Date: Mar. 30, 2000

(30) Foreign Application Priority Data

Sep. 18, 1998 (FR) .................................. 98 11703

(51) Int. Cl.⁷ ............................................. A61B 17/70
(52) U.S. Cl. ....................................................... 606/61
(58) Field of Search ...................... 606/59–61; 403/362

(56) References Cited

U.S. PATENT DOCUMENTS

| | | | |
|---|---|---|---|
| 5,374,267 A | * 12/1994 | Siegal | 606/61 |
| 5,413,576 A | 5/1995 | Rivard | |
| 5,542,946 A | * 8/1996 | Logroscino et al. | 606/61 |
| 5,810,815 A | * 9/1998 | Morales | 606/61 |
| 5,989,251 A | * 11/1999 | Nichols | 606/61 |

FOREIGN PATENT DOCUMENTS

| | | | |
|---|---|---|---|
| EP | 0558121 | 9/1993 | |
| FR | 2642642 | 8/1990 | |
| FR | 2697992 | 5/1994 | |
| FR | 2702363 | * 9/1994 | 606/60 |

* cited by examiner

Primary Examiner—Kevin Shaver
Assistant Examiner—Michael B. Priddy
(74) Attorney, Agent, or Firm—Dowell & Dowell, P.C.

(57) ABSTRACT

A posterior spinal osteosynthesis device for providing a transverse connection between two vertebral rods extending along a spinal segment wherein the device includes pairs of hooks adapted to laterally engage the vertebra with each pair being connected by a pair of parallel rods which are elastically bent to form a transverse arc whose ends are engaged in bores within the hooks.

16 Claims, 10 Drawing Sheets

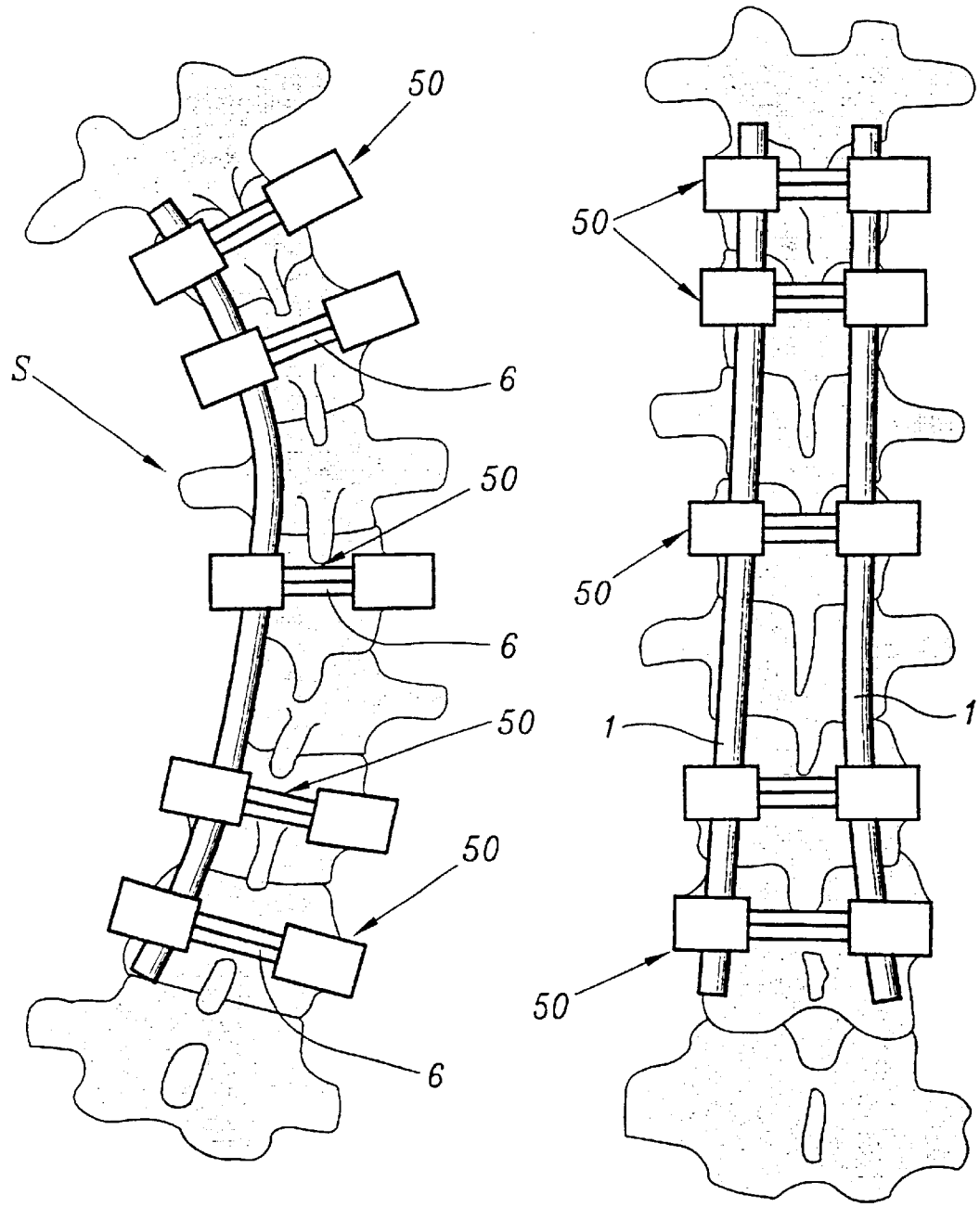
FIG.1  FIG.2

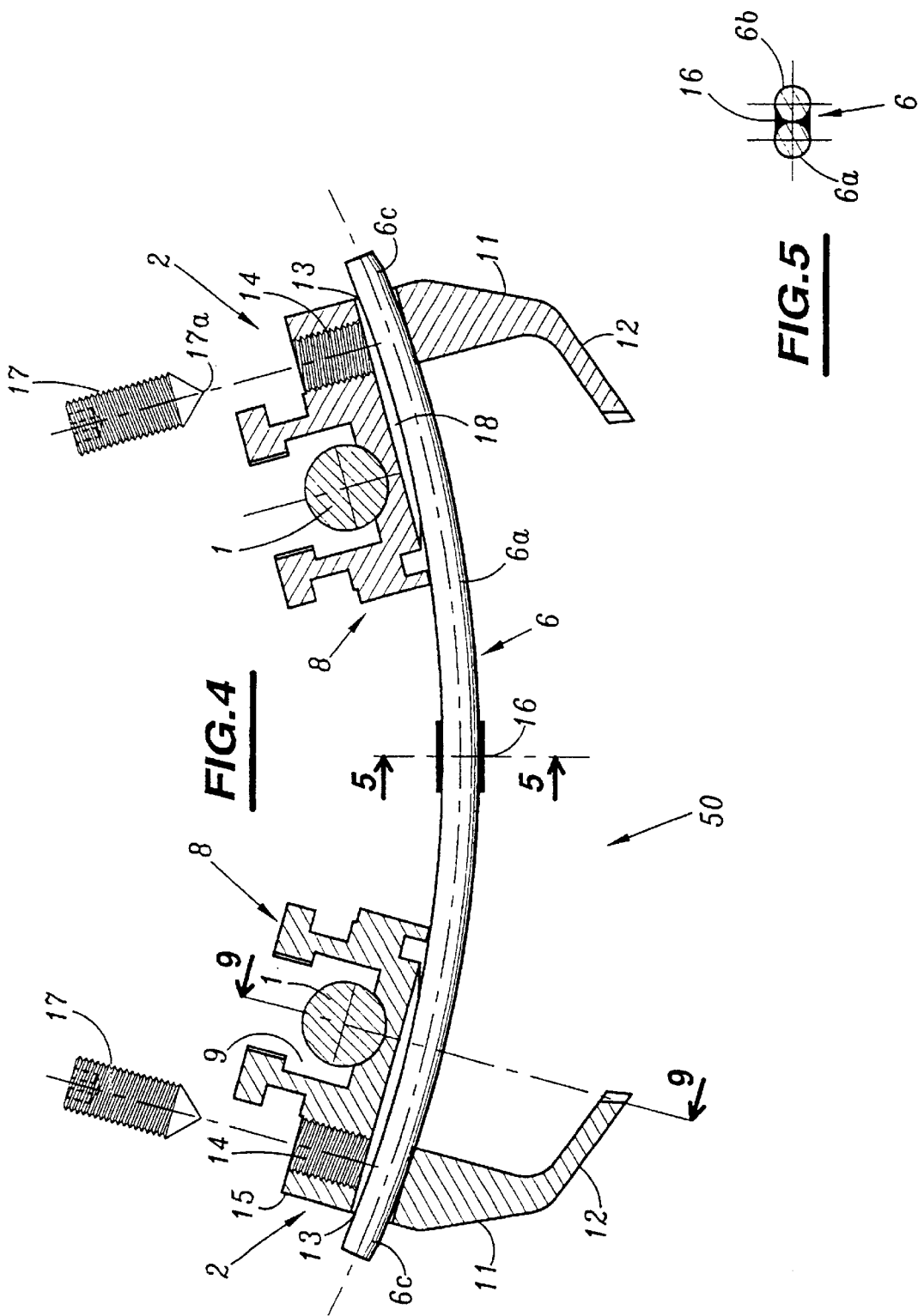

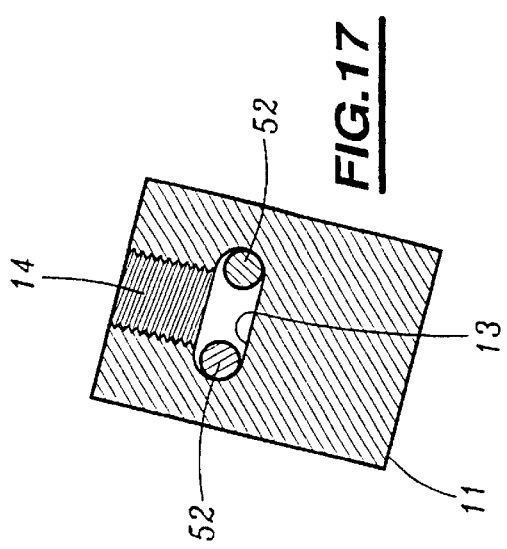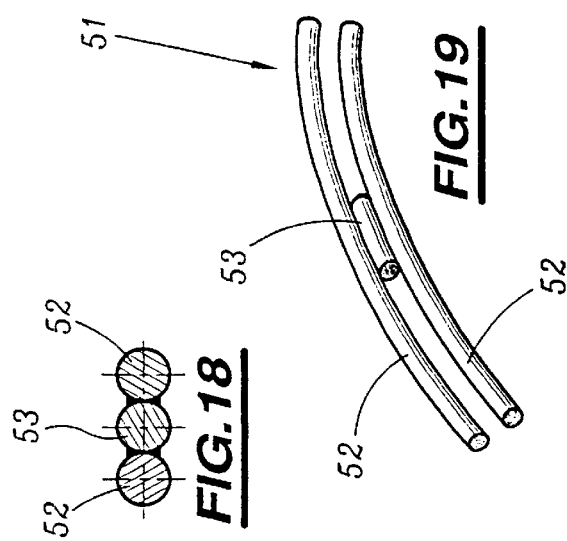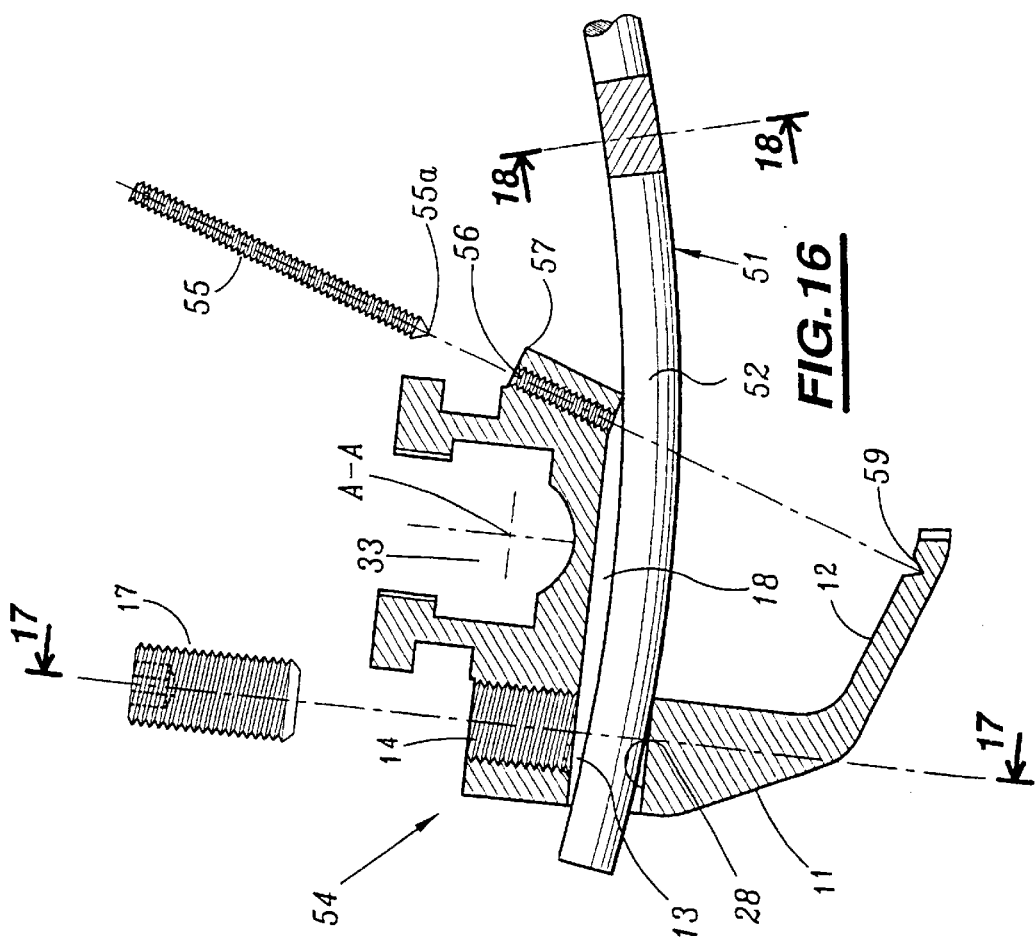

POSTERIOR BACKBONE OSTEOSYNTHESIS DEVICE

BACKGROUND OF THE INVENTION

1. Field of the Invention

The present invention relates to a posterior spinal osteosynthesis device intended to ensure a transverse connection between two vertebral rods extending along a spinal segment.

Such a device is of the type comprising a pair of hooks bearing laterally on a vertebra, and fixed to a means for connecting them to each other.

2. Description of the Related Art

International patent application WO 97/25931 describes a posterior transverse connection device in which two hooks are connected via a tubular element passing through a central piece placed above the spinous process of the vertebra, this central piece serving as a bearing for longitudinal rods.

When orthopedic surgeons wish to correct scoliosis, they can use pedicular screws in the area of the lumbar vertebrae by virtue of the fact that the dimensions of the pedicles of these vertebrae are sufficient for screws. By contrast, in the area of the thoracic vertebrae which are thinner than the lumbar vertebrae, the space available is rarely sufficient for screws, and this forces the surgeons to use pedicular hooks connected to transverse hooks.

When the scoliosis is pronounced, the surgeon experiences difficulties in displacing the vertebra to the desired position with the aid of hooks. This is because the vertebra must be displaced in translation in the frontal plane and in rotation in the sagittal plane by pivoting on itself. This results in a risk of sliding of the hooks on which the surgeon is exerting pressure. In brief, if the surgeon only has to exert a restoring force on the vertebra, a single hook may suffice. By contrast, if the vertebra must additionally turn about itself, the surgeon places a second transverse pedicular hook on the other side of the pedicle, with a connection rod passing through the two hooks, which reduces the risk of these sliding. The fact remains, however, that this risk exists because of the insufficient hold provided by the hooks.

Moreover, the hooks are adjusted as best as possible on the vertebrae without being fixed thereto. This results in an appreciable play and therefore poor bone anchoring, and this means that the restoring couple must not be too high. Furthermore, the positioning of the hooks and of the screws takes a long time and disadvantageously prolongs the time needed for the surgical intervention.

Finally, the various pedicular hooks, both transverse and laminar, are not effective in the maneuvers of rotational correction of the position of the vertebrae, their action on these vertebrae being limited to displacements in the postero-anterior or antero-posterior directions. In addition, the blade of the laminar hooks is in contact with the dura mater in the medullary canal.

The vertebral screws of the known instrument systems also present a not inconsiderable risk of touching the spinal cord when they are being fitted by the surgeon, besides the fact that they require pedicles of sufficient size.

SUMMARY OF THE INVENTION

The object of the invention is to make available a posterior spinal osteosynthesis device of the type mentioned above which is made in such a way as to permit a solid hold of the hooks on the vertebra, sufficient to eliminate any risk of sliding or tilting of the hooks during a movement of rotation imparted to the vertebra in order to correct a scoliosis.

According to the invention, the body of the hooks is designed to bear on transverse processes of the vertebra which have been resected beforehand, and the connection means consists of a pair of parallel rods which are joined together and bent elastically to form a transverse arc whose ends engage in bores formed in the hooks, and means are provided for fixing the hooks to the ends of the rods of the transverse arc in positions generating elastic restoring couples via the vertebral arc of the hooks bearing on the transverse processes.

To prepare for fitting such a device, the surgeon resects two transverse processes (or apophyses) at the appropriate site, which frees an accessible space between the resected face of each transverse process and the corresponding side when the vertebra is a thoracic vertebra. Although the first application of the device according to the invention is intended for the thoracic vertebrae, this device can also be fitted equally well on the other vertebrae, in particular the lumbar vertebrae.

Once the two hooks are in place on the transverse arc, which is bent elastically, the surgeon then uses a suitable clamp to tighten the two hooks bearing on the transverse processes, in order to slide them on the transverse arc and move them toward each other, which accentuates the curvature of the rods of the arc, which remains in its elastic range. The hooks are then locked on the arc. The latter then exerts on the hooks a restoring couple which keeps them firmly applied on the transverse processes. This thus affords a solid assembly in which the hooks do not slip on the vertebra under the forces which are imparted to them by the surgeon in order to pivot the vertebra, and they subsequently remain in place without play.

The vertebral arc advantageously consists of two welded cylindrical rods instead of one. This is because the use of a single rod would involve a risk of rotation of one hook on the rod relative to the other, whereas two parallel and integral rods prevent any tilting of the hooks on the transverse arc.

The bodies of the hooks are of whatever form but preferably delimit a U-shaped channel adapted to receive the vertebral rod and are provided with suitable means for locking the rod on the hook.

The device according to the invention permits arthrodesis of two or more vertebrae using at least two connection devices of this type connected to two vertebral rods.

According to one characteristic of the invention, the bores of the hooks have an oblong cross section complementing that of the cylindrical rods of the transverse arc.

According to one embodiment of the invention, each hook comprises a body designed to receive the corresponding vertebral rod, and a lateral stem adapted to be able to bear on the transverse process, and the oblong bore is formed at the junction between the body and the stem so as to be traversed by the end of the transverse arc; a threaded hole formed in the stem opens into the oblong hole, this threaded hole being adapted to be equipped with a screw for blocking the hook on the transverse arc.

The two rods of the transverse arc can be joined together by any suitable means, for example by laser welding.

BRIEF DESCRIPTION OF THE DRAWINGS

Other particularities and advantages of the invention will become evident from the following description in which reference is made to the attached drawings which illustrate several embodiments thereof as nonlimiting examples.

FIG. 1 is a diagrammatic elevation showing spinal osteosynthesis instrumentation provided with transverse connection devices according to the invention and placed on a spinal segment affected by scoliosis, before correction of the latter.

FIG. 2 is a view analogous to FIG. 1 and shows the completed instrumentation on the spinal segment in which the scoliosis has been corrected.

FIG. 4 is a longitudinal section, on an enlarged scale, through the osteosynthesis device in FIG. 3.

FIG. 5 is a transverse section along 5—5 in FIG. 4.

FIG. 16 is a partial view, half in section and half in elevation, of a sixth embodiment of the device according to the invention.

FIG. 17 is a section along 17—17 in FIG. 16.

FIG. 18 is a transverse section along 18—18 in FIG. 16.

FIG. 19 is a perspective view of the transverse arc of the device in FIGS. 16 to 18.

DESCRIPTION OF THE PREFERRED EMBODIMENTS

Figure 3:
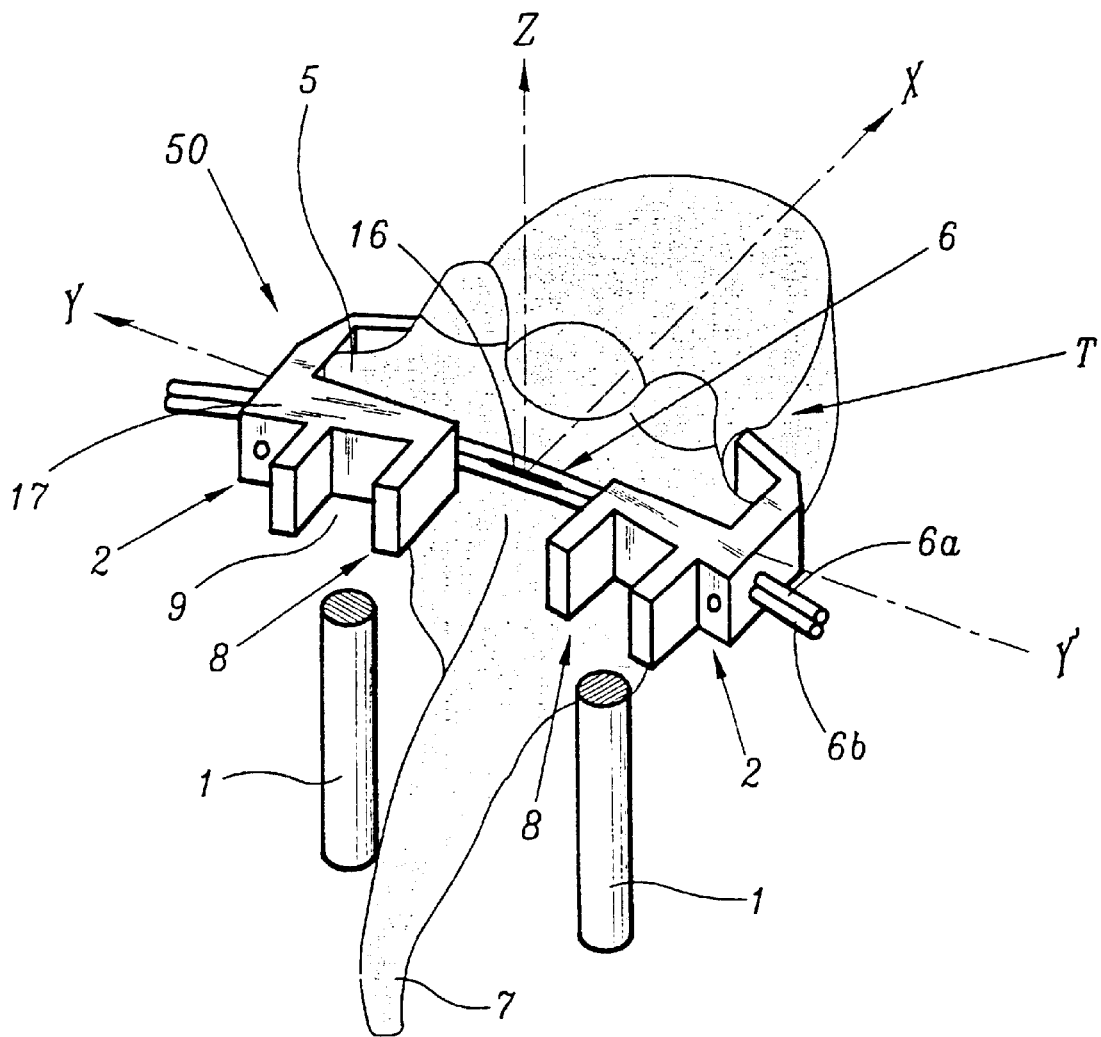
FIG. 3 is a perspective view, substantially to scale, of a first embodiment of the posterior spinal osteosynthesis device according to the invention, implanted on a vertebra.

The posterior spinal osteosynthesis instrumentation illustrated in FIGS. 1 and 2 is intended to correct vertebral deviations such as scoliosis of a spinal segment S in order to straighten the latter to the position in FIG. 2.

This instrumentation comprises two posterior longitudinal vertebral rods 1, extending along the segment S on each side of the spinous processes, and a set of transverse connection devices 50 between the rods 1, which are suitably distributed between the ends thereof in order to confer sufficient rigidity to the assembly.

Each device 50 comprises a pair of transverse hooks 2, each traversed by a vertebral rod 1, and a transverse connection arc 6 between the hooks 2.

The posterior spinal osteosynthesis device illustrated in FIGS. 3 to 9 is intended to ensure a transverse connection between two vertebral rods 1 extending along a spinal segment of at least two vertebral stages.

Each device 50 comprises a pair of hooks 2 bearing laterally on a vertebra, which can be a thoracic vertebra T arranged between two ribs 3 of the thoracic cage, as is represented in FIGS. 2 to 8, or else a vertebra of any spinal segment, for example a lumbar vertebra (FIGS. 1 and 2). These hooks 2 are arranged to the sides of the vertebra, and they are designed in such a way as to be able to bear on previously resected plane faces 4 of the transverse processes (or apophyses) 5 of the vertebra T. The device is completed by a transverse connection arc 6 between the two hooks 2, the opposite ends of which arc 6 are joined to the hooks. The transverse arc 6 bears in its central zone on the base of the spinous process 7 of the vertebra T.

Each hook 2 comprises a body 8 of substantially U-shaped cross section delimiting an inner channel 9 in which a vertebral rod 1 can be arranged. The U-shaped body 8 can be configured in accordance with numerous alternatives, for example as described in French patent 2 697 992 (92 13 868) in the name of EUROSURGICAL. Each hook 2 is provided with means for locking the vertebral rod 1 in the body 8, and these means can for example be similar to those described in the aforementioned French patent.

Each body 8 is continued by a lateral stem 11 intended to be positioned opposite the resected face 4 of the transverse process 5 in order to be able to bear on the latter. For this purpose, the stem 11 extends in a direction almost parallel to a plane containing the longitudinal axis of the vertebral rod 1 and terminates in a curved end 12 forming a securing blade. The blade 12 is configured to be able to extend under the transverse process 5, while the body 8 is positioned posterior to this transverse process, nearer the spinous process 7. The terminal blade 12 forming a hook is rectilinear and forms, with the stem 11, an obtuse angle which can vary substantially depending on the anatomical shape of the vertebra.

Formed in each hook 2 there is a bore 13 of oblong cross section which, at the junction of the stem 11 and of the body 8, extends in the transverse direction, substantially perpendicular to the longitudinal axis of the channel 9. Opening into this oblong bore 13 there is a threaded hole 14 which has been machined in a lateral part 15 protruding from the body 8 and constituting the base of the stem 11.

The transverse arc 6 consists of two parallel metal rods 6a, 6b which are joined together, for example by laser welding, in their central zone 16. The two rods 6a, 6b are made of a suitable metal, are bent elastically and extend under the body 8 of the hooks 2 forming an arc whose opposite ends 6c engage in the oblong bores 13, the cross section of which complements the circumference of the two rods 6a, 6b.

The hooks 2 are locked on the ends 6c of the arc 6 by means of locking screws 17 which are screwed into the holes 14 until their point 17a engages between the two rods 6a, 6b and thus locks the respective hooks 2 on the transverse arc 6, after the surgeon has suitably positioned the hooks 2 on the arc 6.

In each hook 2, the oblong bore 13 is continued via a longitudinal clearance 18 (FIGS. 3 and 5) which is machined in the face of the body 8 remote from its channel 9 and constitutes a sort of slide making it easier to fit the transverse arc 6.

The transverse processes 5 are partially ablated in advance so that the stem 11 and the hook blade 12 can respectively bear against the remaining transverse portion 5 and reach the pedicles of the vertebra T via the side.

Figure 6:
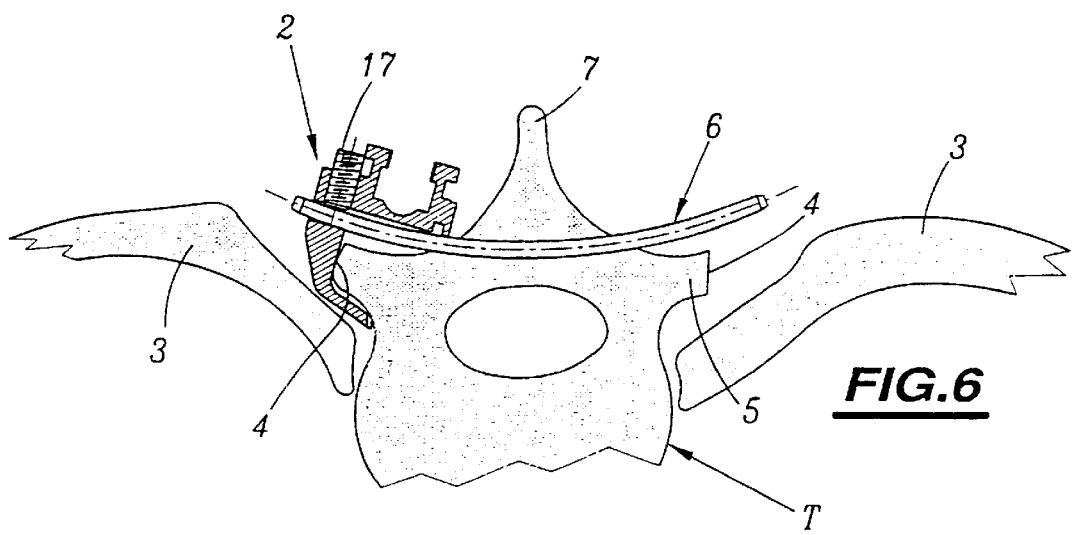
FIGS. 6, 7 and 8 are longitudinal sections analogous to FIG. 5, illustrating a sequence of implantation of the osteosynthesis device on a thoracic vertebra.
Figure 7:
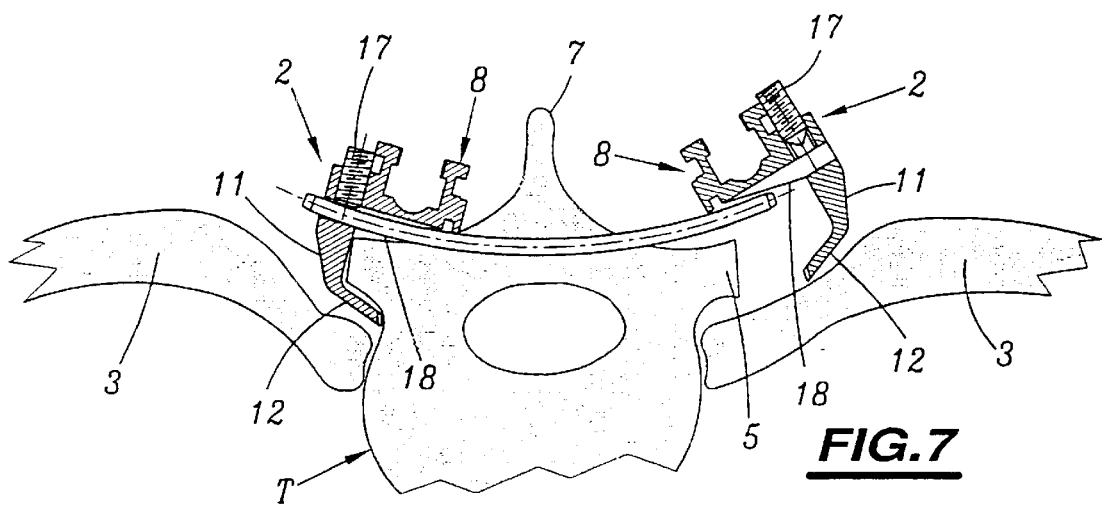
Figure 8:
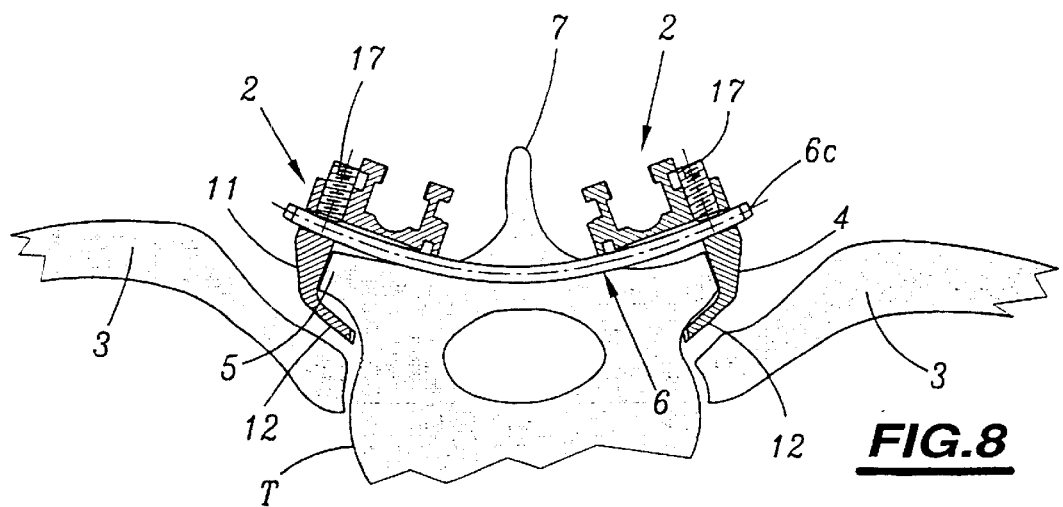
Figure 9:
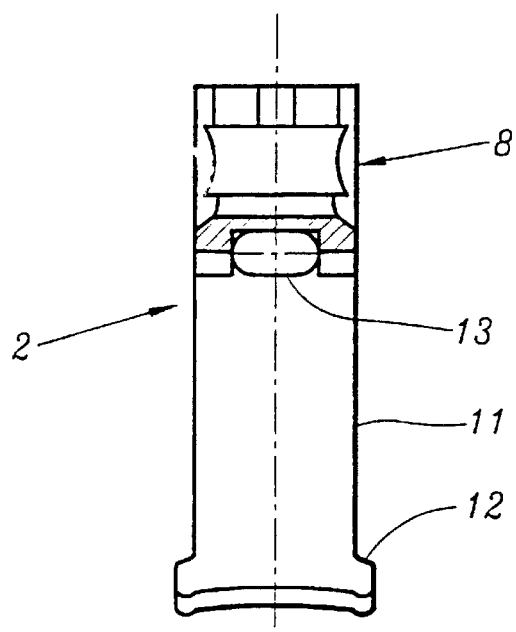
FIG. 9 is a transverse section along 9—9 in FIG. 4.

FIGS. 6 to 8 illustrate an operating sequence for implanting the transverse connection device according to the invention on a thoracic vertebra T.

Having partially ablated the transverse processes 5 in order to obtain resected faces 4, the surgeon engages a hook 2 on one end of the transverse arc 6, on which he positions it by tightening the screw 17. The surgeon then introduces the assembly of hook 2 and arc 6 onto the vertebra T, enclosing the remaining transverse portion 5 on the side in question, as is illustrated in FIG. 4. Depending on the clinical circumstances, the stem 11 and/or the end blade 12 of the hook 2 come into contact with the remaining transverse portion 5 and/or with the pedicles of the vertebra T. The surgeon engages the second hook 2 on the other end 6c of the transverse arc 6 (FIG. 5), introducing the end 6c into the oblong bore 13 until the hook 2 in turn comes into lateral abutment with the other pedicle of the vertebra T and/or the other remaining transverse portion 5.

The final maneuver by the surgeon, illustrated in FIG. 8, consists in sliding the second hook 2 onto the transverse arc 6, moving the two hooks toward one another. The terminal blades 12 being in bilateral contact at the level of the pedicles of the vertebra T, the sliding of the hooks on the arc 6 is obtained by the surgeon by means of a clamp (not shown) which allows the two hooks to be moved toward one another and forces the transverse arc 6 to bend more, while remaining in its elastic range (FIG. 8). After screwing the locking screws of each hook on the arc 6, the latter thus exerts on the hooks 2 restoring couples corresponding to its tendency to recover its initial curvature. These restoring couples tend to tighten the hooks 2 against the pedicles and/or the remaining transverse portions 5 and thereby reinforce the hold of the hooks 2.

The transverse connection device according to the invention thus ensures stable osseous anchoring in an entirely satisfactory manner on the vertebra T on which it is implanted, and is easy to use.

Figure 10:
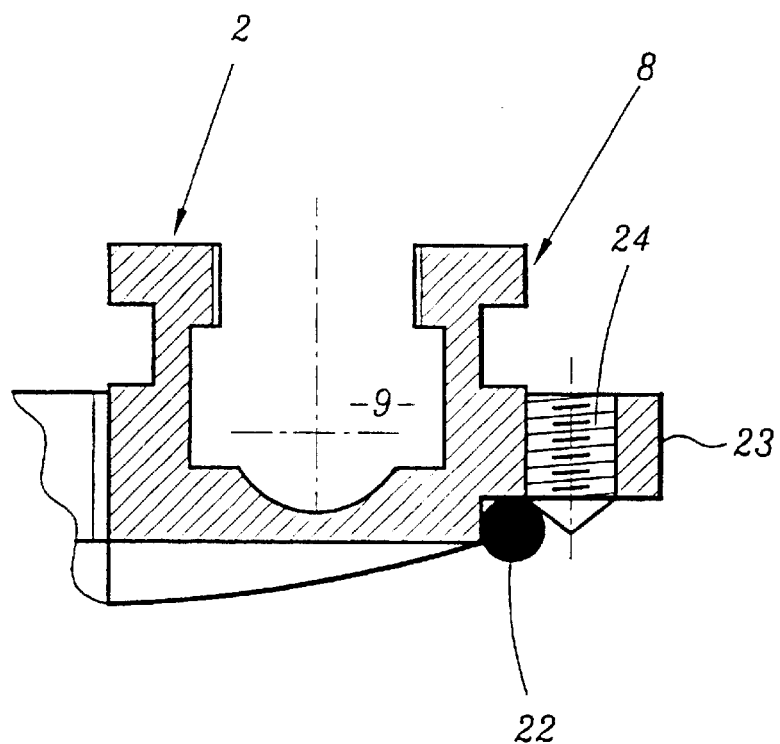
FIG. 10 is a partial section, on an enlarged scale, through a hook according to a second embodiment of the device used in the invention.
Figure 11:
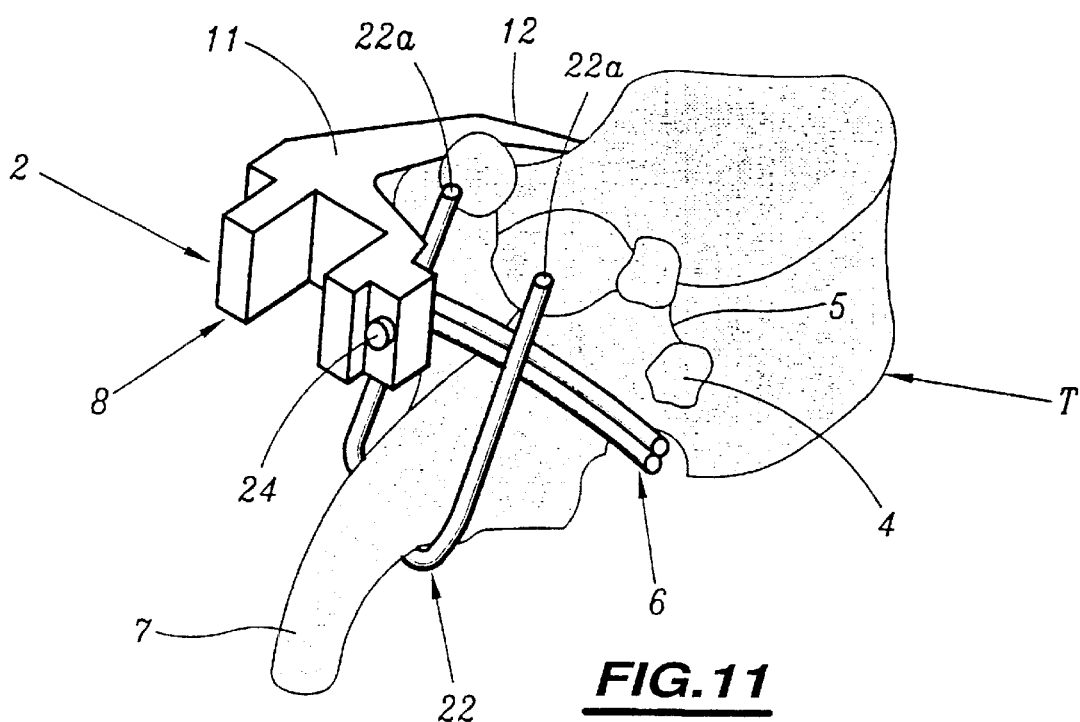
FIG. 11 is a partial perspective view of the osteosynthesis device according to the second embodiment in FIG. 10, placed on a vertebra.

In the second embodiment of the invention, illustrated in FIGS. 10 and 11, the device is provided with a secondary arc 22 consisting of a substantially U-shaped wire adapted to pass under the at spinous process 7 of the vertebra T. The branches 22a of the secondary arc 22 bear under the bodies 8 of the hooks 2 and exert on the transverse arc 6 restoring couples which allow it to be pressed against the spinous process 7. More precisely, each branch 6a bears on a lateral extension 23 of the body 8 of the hook 2 and on the wall of the body 8 and is held there by suitable blocking means such as a locking screw 24 inserted into each extension 23.

With this alternative embodiment it is possible to improve the stability of the device, particularly in respect of the rotation about the axis Y–Y' (FIG. 3), this axis being horizontal and situated in the frontal plane. As a result of the restoring couples exerted on the transverse arc 6, the secondary arc 22 applies the latter against the upper part of the spinous process 7 and applies the whole of the device on the vertebra and consequently counters any tilting about the axis Y–Y' relative to the vertebra.

The device according to the invention also has the advantage of being in removable and permanent connection with the vertebra. In addition, the use of an elastic arc 6 with quite a considerable potential deformation allows the hooks 2 to remain in contact with the bone despite possible variation in the force at the interface between bone and hook 2, which could result in relaxation of the bone under the clamping force for example.

The implantation can be accompanied by bone grafts, without any need to subsequently remove the device. However, such disassembly is easy to perform by unscrewing the locking screws 17.

Figure 12:
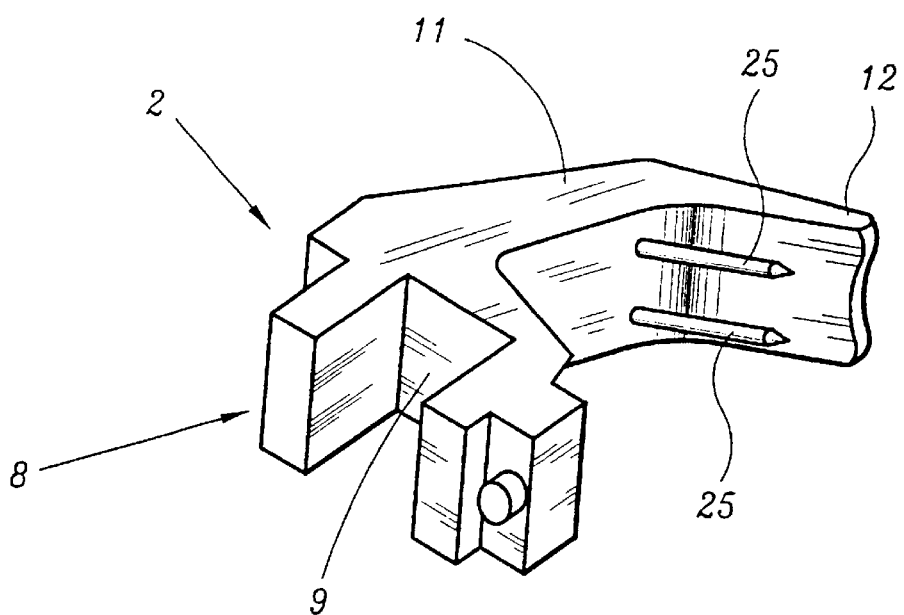
FIG. 12 is a perspective view, on an enlarged scale, of a third embodiment of the hook of the device according to the invention.

In the third embodiment of the device, illustrated in FIG. 12, each hook is equipped with points 25, for example two in number, as shown, which project from the stem 11 between the body 8 and the curved blade 12. These pointed elements 25 penetrate the spongy substance of the portion of the corresponding remaining transverse processes 5 when the hooks 2 are placed on the vertebra T in the manner described above. This embodiment constitutes another way of improving the stability of the device on the vertebra T, in particular for preventing any rotation about the axis Y–Y' of the device relative to the vertebra.

In the various embodiments described above, the body of the stem 11 bears on the truncated face 4 of the transverse process 5 when the device is put into place, whereas the curved end 12 forming the blade is adapted to extend along said transverse process 5.

Figure 13:
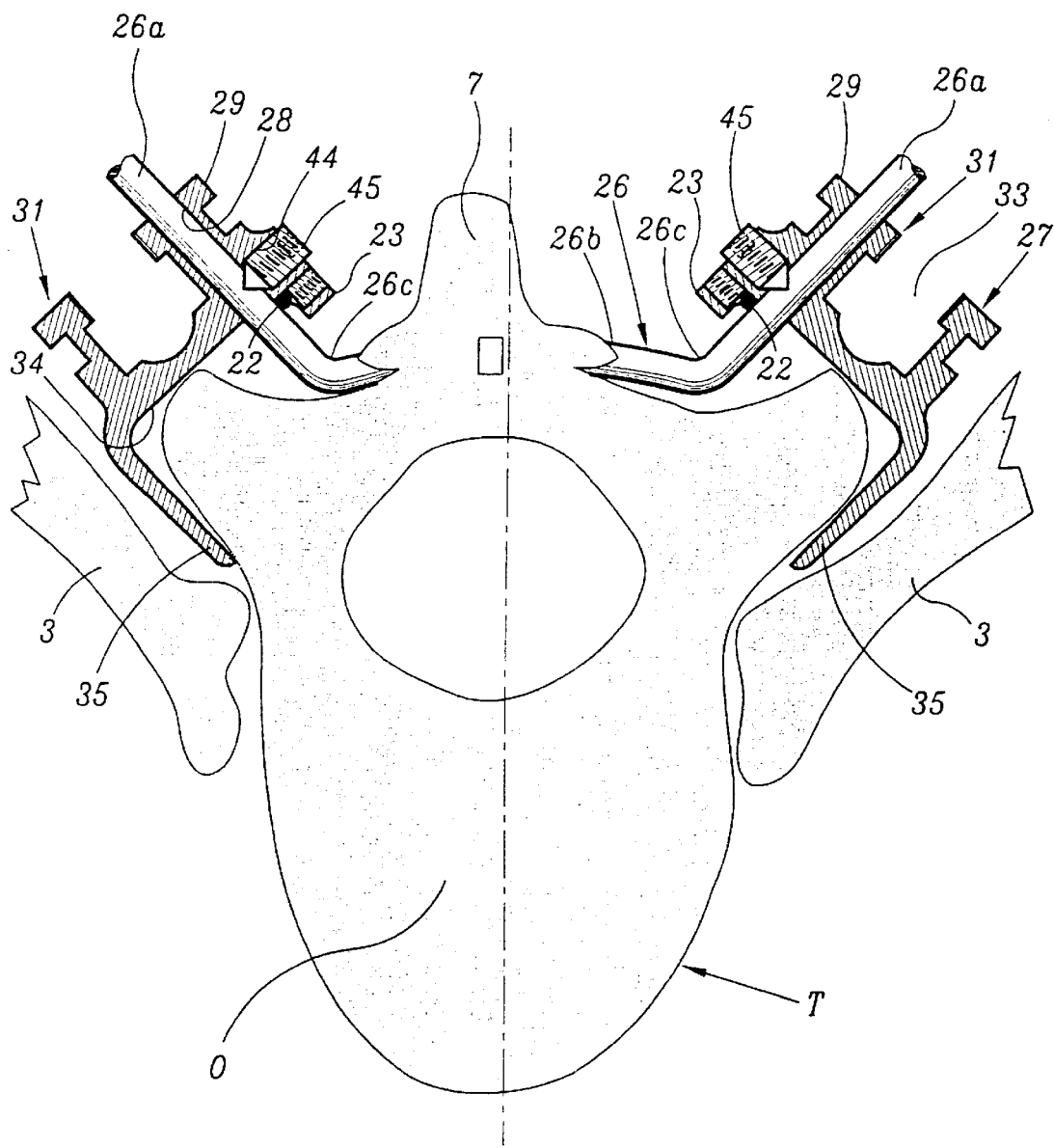
FIG. 13 is a transverse section, on an enlarged scale and in a horizontal plane, of a fourth embodiment of the osteosynthesis device according to the invention, implanted on a vertebra.

The fourth embodiment of the device, illustrated in FIG. 13, differs from the preceding ones in that the transverse arc 26, formed by two wires as before, has a triple curvature in a horizontal plane in order to allow it to better adapt to the anatomical shapes of the posterior arch of the vertebra T. More precisely, between its rectilinear ends 26a inserted in the respective hooks 27, the transverse arc 26 comprises a concave central part 26b whose concavity substantially matches the convexity of the posterior arch of the vertebra, and two convex lateral parts 26c which connect the central part 26b and the rectilinear end parts 26a.

Each end 26a of the arc 26 is lodged in a bore 28 formed in a branch 29 of the body 31 of the hook 27, the second branch 32 delimiting with the branch 29 the U-shaped channel 33 for receiving the vertebral rod 1. The bottom 34 of the body 31 extends opposite the resected transverse process 5 when the device is in place. The body 31 is continued laterally by a substantially rectilinear stem 35 which extends almost parallel to the branch 29. When the device is mounted on the vertebra T, the body 31 thus bears on the resected face 4 of the transverse process 5 and the lateral stem 35 extends between the adjacent rib 3 and the side of the transverse process 5.

A threaded hole 44 is formed in the branch 29 of the body 31 and opens into the oblong bore 28. The hole 44 is adapted to receive a screw 45 for blocking the corresponding hook 27 on the transverse arc 26 in the desired position after orientation and sliding of the body 31 on the rectilinear end 26a of the transverse arc 26.

In the fifth embodiment of the device (FIGS. 14 and 15), the transverse arc 26 is made up of two metal wires 38, 39, of which one, for example the wire 39, includes a threaded end 41 extending beyond the smooth end 42 of the wire 38 in such a way as to protrude outside the bore 28. This threaded end 41 is provided with a nut 43 for blocking the corresponding hook 27 on the transverse arc 26.

Of course, the bore 28 has an oblong cross section adapted to that of the two wires 38, 39 arranged side by side. This oblong bore 28 extends in a direction almost parallel to that of the lateral stem 35. The nuts 43 permit both sliding and blocking of the two hooks 27 on the transverse arc 26.

Figure 14:
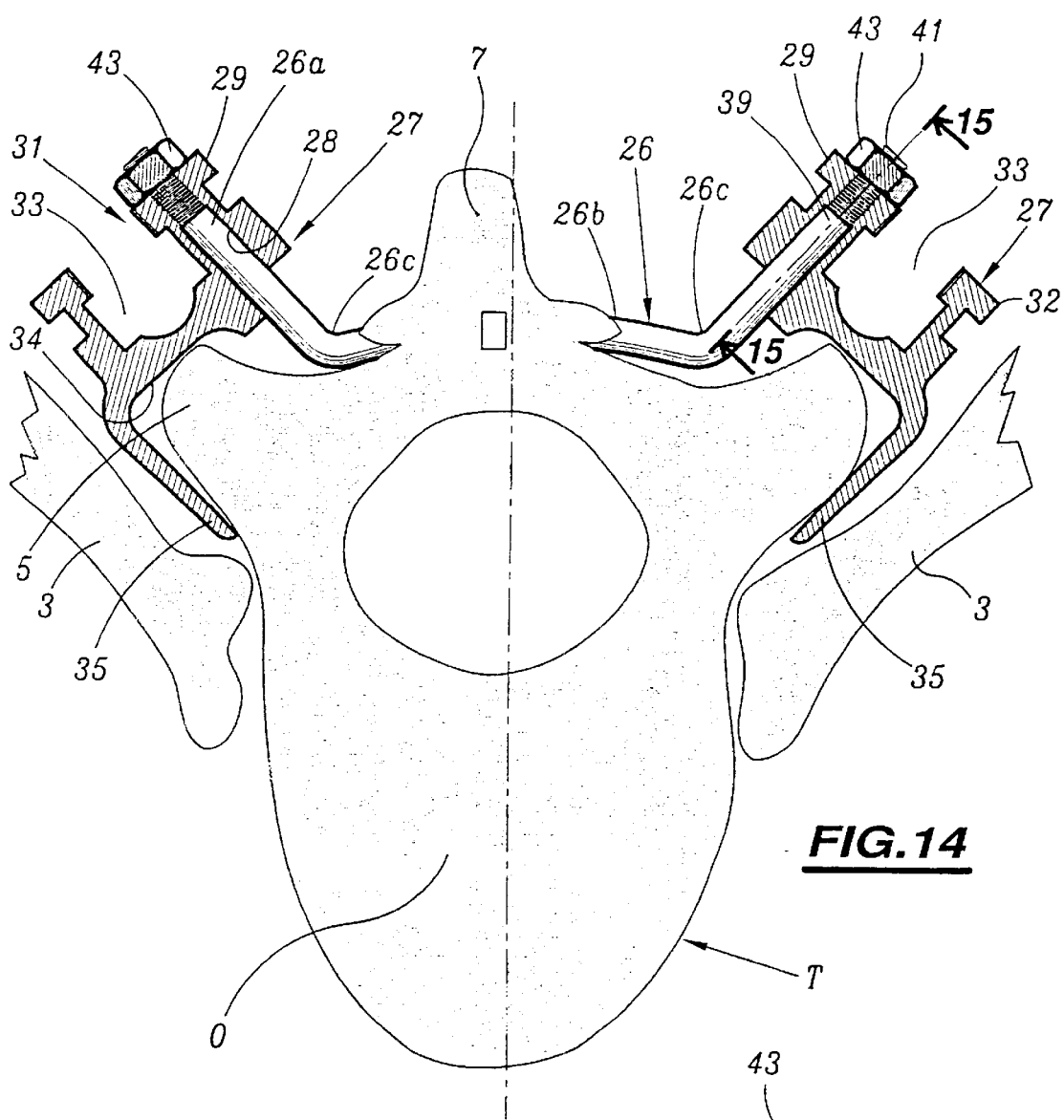
FIG. 14 is a view analogous to FIG. 12 illustrating a fifth embodiment of the device according to the invention.
Figure 15:
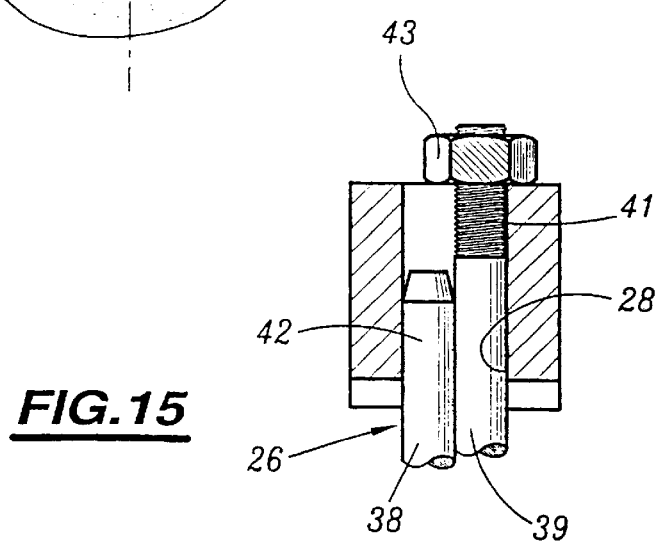
FIG. 15 is a partial section, on an enlarged scale, along line 15—15 in FIG. 14.

The two embodiments in FIGS. 13 to 15 make it possible to limit the posterior space taken up by the device by virtue of the fact that the bodies 31 of the hooks 27 are laterally offset with respect to the faces 4 of the transverse processes 5, and this by virtue of the triple curvature of the transverse arc 26. In addition, the bodies 31 of the hooks are at the same time distant from the instantaneous center of rotation O of the vertebra T, which fact increases the leverage and thus reduces the stresses caused to develop in the event of a force straightening the vertebra.

According to the sixth embodiment represented in FIGS. 16 to 19, the transverse arc 51 consists of three rods, namely two long outer rods 52 and one short central rod 53 welded to the other two, for example by laser. Each associated hook 54 is equipped with a screw 55 which can be screwed into a threaded bore 56 machined in a lateral reinforcement 57 of the body of the hook 54. The longitudinal axis of the bore 56 is inclined with respect to the longitudinal axis A—A of the channel 33 of the hook 54, and the screw 55 has a length which is such that, after being screwed into the bore 56, it can pass through the corresponding transverse process 5 and its point 55a comes into abutment in a recess 59 formed in the end of the curved blade 12.

By virtue of the spacing between the two rods 52, the transverse arc 51 allows the screw 55 to pass between these, and said screw 55 passes through the remaining portion of the transverse process 5 in a direction substantially perpendicular to the main axis of said transverse process.

In addition, by virtue of the supplementary screw 55, this embodiment makes it possible to better stabilize the transverse connection device relative to the vertebra T, particularly as regards rotation about the axis Y–Y' and translation on the axis Z. The tightening screw 17 still ensures blocking of the hook 54 relative to the arc 51, even though the rods 52 are no longer joining as in the device in FIGS. 3 to 9.

Figure 20:
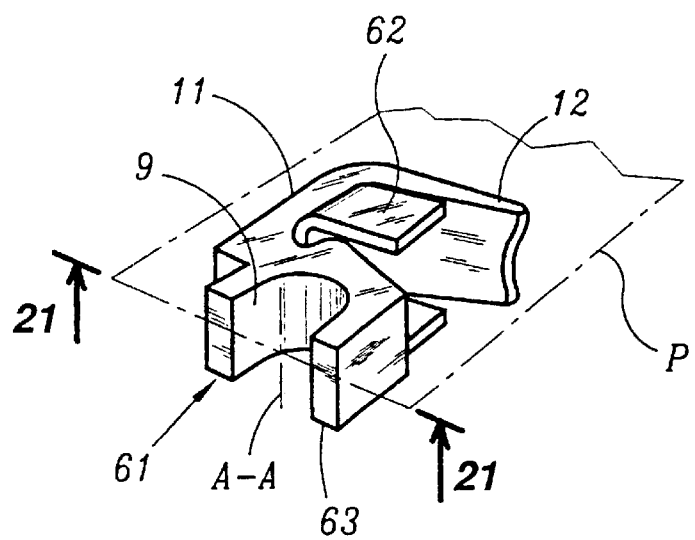
FIG. 20 is a perspective view of a hook according to a seventh embodiment.
Figure 21:
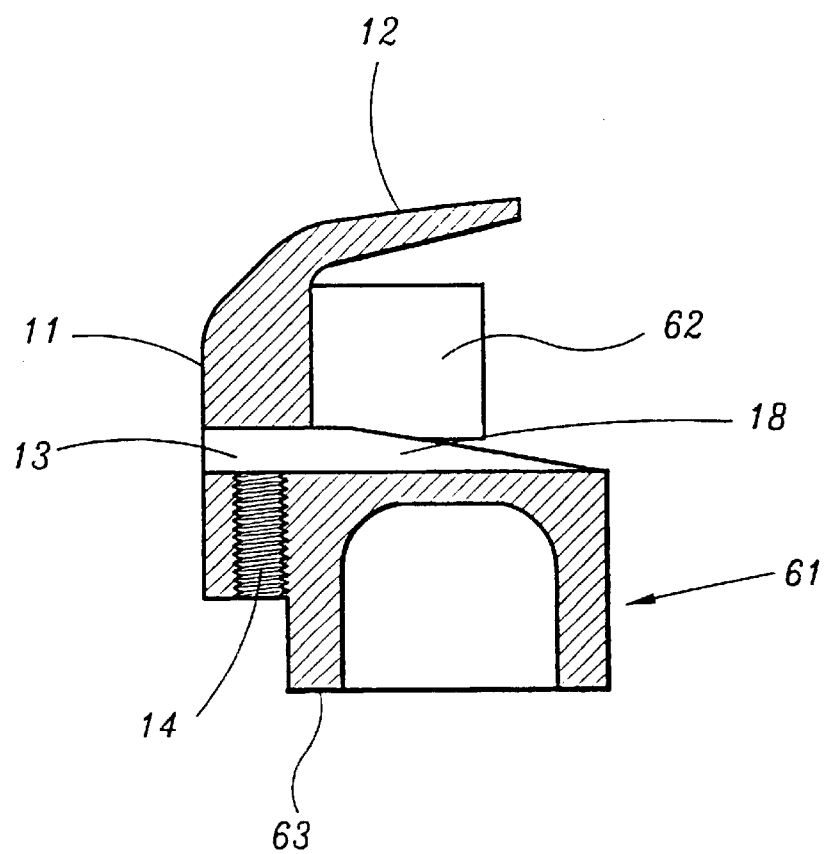
FIG. 21 is a cross section of the hook according to 21—21 in FIG. 20.

The embodiment of the hook 61 illustrated in FIGS. 20 and 21 differs from the preceding ones in that the hook 61 is provided with two panels 62 which form parallel tongues arranged symmetrically with respect to a plane of symmetry P of the hook 61, and which extend from its stem 11 between its body 63 and the curved blade 12. The panels 62 thus also extend almost perpendicular to the longitudinal axis A—A of the U-shaped channel 9 of the hook 61. At least some of the hooks of the transverse connection devices forming part of the osteosynthesis instrumentation according to the invention can be modified in this way.

The addition of the panels 62 avoids any risk of translation of the transverse connection device upward or downward, that is to say along the axis Z. The remaining portions of the transverse processes 5 are thus "embedded" in a small cavity delimited by the panels 62, the blade 12 and the base of the body 63 of the hook 61.

The invention is not limited to the embodiments described and can include many alternatives. For example, the number of pointed elements 25 can vary, the minimum being one.

It should also be noted that the embodiments in FIGS. 10 to 12 can be combined with the variants in FIGS. 13 to 15.

What is claimed is:

1. A posterior spinal osteosynthesis device comprising; at least two pairs of hook members and two vertebral rods adapted to be received in a channel defined in a frontal body portion of each hook member, each hook member including a stem extending rearwardly relative to said frontal body portion and in a plane extending generally transversely to longitudinal axes of the two vertebral rods, the stems being oriented to be adapted to bear laterally on transverse processes of a vertebra, a pair of parallel rods which are joined together and bent elastically to form a generally transverse arc extending between each pair of hook members, each pair of parallel rods having ends which engage in bores formed in each hook member, and securing means for securing the hook members to the ends of the parallel rods of the transverse arc so as to create an elastic restoring force by way of the transverse arc and the hook members which are adapted to bear on the transverse processes.

2. The device as claimed in claim 1 wherein the bores have an oblong cross section.

3. The device as claimed in claim 2 wherein the bores are formed between the frontal body portion and the stem of each hook member, each securing means including a threaded hole formed in each stem which opens into an adjacent one of the bores bore, and each threaded hole being adapted to receive a screw for securing the hook member on the transverse arc.

4. The device as claimed in claim 3 wherein each stem is provided with an angled end portion forming a blade adapted to extend along a resected transverse process when another portion of the stem bears on a truncated face of the transverse process.

5. The device as claimed in claim 4, including a secondary arc including a substantially U-shaped wire associated with each pair of hook member which wire is adapted to pass under a spinous process of the vertebra and having spaced branches adapted to bear under the frontal body portion of each pair of hook members so as to exert on the transverse arc a force which presses the parallel rods of the transverse arc against the spinous process.

6. The device as claimed in claim 5 wherein the branches of each said secondary arc bear on lateral extensions of the frontal body portion of each pair of hook members and are by locking means inserted through the extensions.

7. The device as claimed in claim 6 wherein at least one point extends from the stem of each of the hook members.

8. The device as claimed in claim 4 wherein at least one of the transverse arcs includes a central rod welded between the pair of parallel rods, the central rod being shorter than the parallel rods, at least one hook member including a lateral reinforcement extending from the frontal body portion, a threaded bore extending through the lateral reinforcement, and a screw receivable within the threaded bore and having a pointed end which extends between the parallel rods into abutment in a recess in the blade of the at least one hook member.

9. The device as claimed in claim 4 wherein at least one of the hook members is provided with two panels arranged symmetrically with respect to a plane of symmetry (P) of the at least one hook member, and which panels extend from the stem between the frontal body portion and the blade.

10. The device as claimed in claim 3 wherein each hook member includes at least one point projecting from its stem adapted to engage in the transverse process.

11. The device as claimed in claim 1 wherein the two parallel rods of the transverse arc are joined together by a weld joint.

12. The device as claimed in claim 1 wherein the transverse arc has a triple curvature in a plane so as to adapt to an anatomical shape of a posterior arch of the vertebra the ends of the transverse arc being rectilinear and extending outwardly relative to a concave central part.

13. The device as claimed in claim 12 each bore is formed in a branch of the frontal body portion of each hook member, and the frontal body portion including a lateral stem which is adapted to bear against the transverse process.

14. The device as claimed in claim 13 wherein the branch of the frontal body portion of each hook member includes a threaded hole opening into the bore thereof and adapted to receive a screw for securing the hook member on the transverse arc.

15. The device as claimed in claim 13 wherein one of said parallel rods includes a threaded end extending beyond the end of the other parallel rod in such a way as to protrude outside the bore of the frontal body portion of each hook member, and a nut engageable with the threaded end for securing the hook members on the transverse arc.

16. The device as claimed in claim 1, including a secondary arc including a substantially U-shaped wire associated with each pair of hook members which wire is adapted to pass under a spinous process of the vertebra and having spaced branches adapted to bear under the frontal body portion of each pair of hook members so as to exert on the transverse arc a force which presses the parallel rods of the transverse arc against the spinous process.

\* \* \* \* \*